(12) United States Patent
Sondermeijer et al.

(10) Patent No.: US 7,060,282 B1
(45) Date of Patent: Jun. 13, 2006

(54) ATTENUATED EQUINE HERPESVIRUS

(75) Inventors: Paulus Jacobus Antonius Sondermeijer, Boxmeer (NL); Nicolaas N. Visser, Boxmeer (NL); Cherida Rachel Dhore, Tegelen (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/744,799

(22) PCT Filed: Jul. 26, 1999

(86) PCT No.: PCT/EP99/05476

§ 371 (c)(1),
(2), (4) Date: Apr. 3, 2001

(87) PCT Pub. No.: WO00/08165

PCT Pub. Date: Feb. 17, 2000

(30) Foreign Application Priority Data

Jul. 31, 1998 (NL) ................................ 98202594.2

(51) Int. Cl.
*A61K 39/245* (2006.01)

(52) U.S. Cl. ................................ 424/229.1; 424/204.1; 435/69.1

(58) Field of Classification Search ............. 435/173.3, 435/235.1, 236, 69.1, 91.33, 91.2; 424/204.1, 424/224.1
See application file for complete search history.

(56) References Cited

FOREIGN PATENT DOCUMENTS

| WO | WO 92 01045 | 1/1992 |
|---|---|---|
| WO | WO 96 04394 | 2/1996 |

OTHER PUBLICATIONS

Lewis et al., "Transcriptional control of the equine herpesvirus 1 immediate early gene" Virology, vol. 197, No. 2 Dec. 1993, p. 788-792.

Smith et al., "Nuclear localization and transcriptional activation activities of truncated versions of the Immediate-Early gene product of Equine Herpes 1" Journal of Virology, vol. 69 No. 6, Jun. 1995, p. 3857-3862.

Marshall et al., "An Equine Herpesvirus-1 Gene 71 Deletant is Attenuated and Elicits a Protective Immune Response in Mice" Virology, vol. 231, No. 1, p. 20-27.

*Primary Examiner*—Ali R. Salimi
(74) *Attorney, Agent, or Firm*—William M. Blackstone; William P. Ramey, III

(57) ABSTRACT

The present invention relates to novel Equine herpesvirus (EHV) mutants comprising one or more deletions, substitutions, or insertions in the endogenous promoter region of an essential viral gene, preferably the immediate early gene of EHV. The EHV mutants are stable and have reduced virulence, which makes them very suitable for use in a live vaccine. The invention furthermore relates to live vaccines comprising said EHV mutants, to DNA sequences and vectors harbouring a mutated EHV sequence, to host cells transfected with said DNA or vectors. The invention also relates to a method of attenuating EHV in general, and EHV-1 in particular.

19 Claims, 2 Drawing Sheets

SEQUENCE LISTING

```
<160> NUMBER OF SEQ ID NOS: 3

<210> SEQ ID NO 1
<211> LENGTH: 11
<212> TYPE: DNA
<213> ORGANISM: Herpesvirus

<400> SEQUENCE: 1
taatgaratt c                                                          11

<210> SEQ ID NO 2
<211> LENGTH: 5
<212> TYPE: DNA
<213> ORGANISM: herpesvirus

<400> SEQUENCE: 2 ccaat                                                                  5

<210> SEQ ID NO 3
<211> LENGTH: 2
<212> TYPE: DNA
<213> ORGANISM: Herepsvirus

<400> SEQUENCE: 3 cg                                                                     2
```

ATTENUATED EQUINE HERPESVIRUS

FIELD OF THE INVENTION

The present invention relates to a new Equine herpesvirus (EHV) mutant, to its use in vaccines, to DNA sequences and vectors harbouring a mutated EHV sequence, to host cells transfected with such vectors and to a method of attenuating EHV in general, and EHV-1 in particular.

BACKGROUND OF THE INVENTION

Equine herpesviruses comprise a group of antigenic distinct biological agents which cause a variety of infections in horses, ranging from subclinical to fatal disease.

The Equine herpesvirus is inter alia one of the most common causes of infectious abortions and may account for 15% of all mare abortions that occur during the last six months of pregnancy. Equine herpesvirus type 1 (EHV-1) can cause abortion, perinatal foal mortality, respiratory inflammation and neurologic disease.

Although very similar to EHV-4 (previously classified as EHV-1 subtype 2), EHV-1's main clinical sign is abortion while EHV-4 results in respiratory disease. But both cross over and can be clinically indistinguishable as a disease.

The virus is contracted through inhalation. The respiratory signs can range from severe to inapparent. Abortion occurs primarily in mares over 7 months pregnant, follows infection in 14 to 120 days and can occur suddenly without signs in the mare. The virus infects fetal lung and liver tissue and the mare placental endothelial tissue. Abortion may occur because of direct effects on the fetus or because of placental separation. Near term fetuses may be born alive but due quickly due to lung pathology.

Primary infection of upper respiratory tract of young horses results in a febrile illness which lasts for 8 to 10 days. Immunologically experienced mares may be reinfected via the respiratory tract without disease becoming apparent so that abortion usually occurs without warning. The neurological syndrome is associated with respiratory disease or abortion and can affect animals of either sex at any age, leading to incoordination, weakness and posterior paralyses.

Other EHV viruses are EHV-2 or Equine Cytomegalovirus, which is a ubiquitous antigenically heterogeneous, usually slowly growing group of viruses, causing no-known disease, and EHV-3, the Equine Coital exanthema virus which is the causative agent of a relatively mild pregenital exanthema of both mare and stallion. EHV-1 subtype 2 is now called EHV-4, and is primarily associated with respiratory disease, although sporadic EHV-4 induced abortions have been reported.

The genomic structure of the EHV is similar to that of other alpha herpesviruses, comprising a double stranded linear molecule consisting of two covalently linked segments ($U_L$ and $U_S$), wherein the $U_S$ segment is flanked by inverted repeats. Of the EHV, EHV-1 is the most extensively studied. Telford, E.A.R. et al., Virology 189, 304–316 (1992) have published the complete DNA sequence of EHV-1. The genome consists of about 150,000 bp and about 76 distinct genes have been recognised up to now.

Equine herpesviruses in general and EHV-1 in particular, are ubiquitous pathogens in horses. EHV-1 can even cause epidemics of abortion, respiratory tract disease and central nervous system disorders. Prevention of infection with the virus is therefore of major economic importance, because EHV can be a severe threat, especially to horses living in close groups, such as studs.

Current vaccines against these viruses comprise chemically inactivated viruses or attenuated live viruses. However, these require multiple administration and have only a limited efficacy.

Inactivated vaccines generally induce only a low level of immunity. Attenuated live vaccines are thus preferred because they evoke a more long-lasting immune response and are easier to produce. Attenuation can be obtained by serial passages of virulent strains in tissue culture of other hosts than the natural one. However, the strains thus obtained are not very well defined and were considered not to be effected. Furthermore, there is always a risk that the viruses revert to virulence resulting in disease in inoculated animals. For this reason, genetic attenuation was adopted as a novel approach to obtain safe vaccine strains.

Genetic attenuation consists for example of deletion of one or more non-essential genes. Examples are viruses with deletions in the thymidine kinase gene or the gene encoding glycoprotein gE. Both have been used successfully for genetic attenuation of herpesviruses in general, but similar mutations in EHV-1 strongly abolished replication in the host and made the viruses no longer useful for vaccine purposes. The mutations furthermore often did not result in the desired level of attenuation.

It is therefore a first objective of the present invention to provide new EHV virus strains that do not have the drawbacks mentioned above when used in vaccines.

It is a second objective of the invention to provide a method for the more general genetic attenuation of herpesviruses.

The third objective of the invention is to provide for live vaccines that comprise said novel EHV mutant viruses.

SUMMARY OF THE INVENTION

The first objective of the present invention is achieved by an Equine herpesvirus (EHV) mutant, comprising one or more deletions, substitutions or insertions in the endogenous promoter region of an essential viral gene. Preferably said mutation is a deletion in said endogenous promoter region.

Because attenuation of EHV by mutating non-essential genes was not successful, at least for vaccine purposes, the skilled person would have considered a mutation in the endogenous promoter region of essential genes to be even less promising since one would not have expected the virus to replicate in the host at all. Therefore, the finding of the invention that the endogenous promoter region of essential genes can be mutated to reduce the virulence of EHV viruses leading to a successful attenuation is highly surprising.

The mutations according to the invention do not abolish replication of the virus in the host and affect the level of virulence of the virus. The EHV mutants according to the invention are stable and attenuated with respect to the parent strain, which make them very suitable for use in a live vaccine.

DETAILED DESCRIPTION OF THE INVENTION

Figure 1:
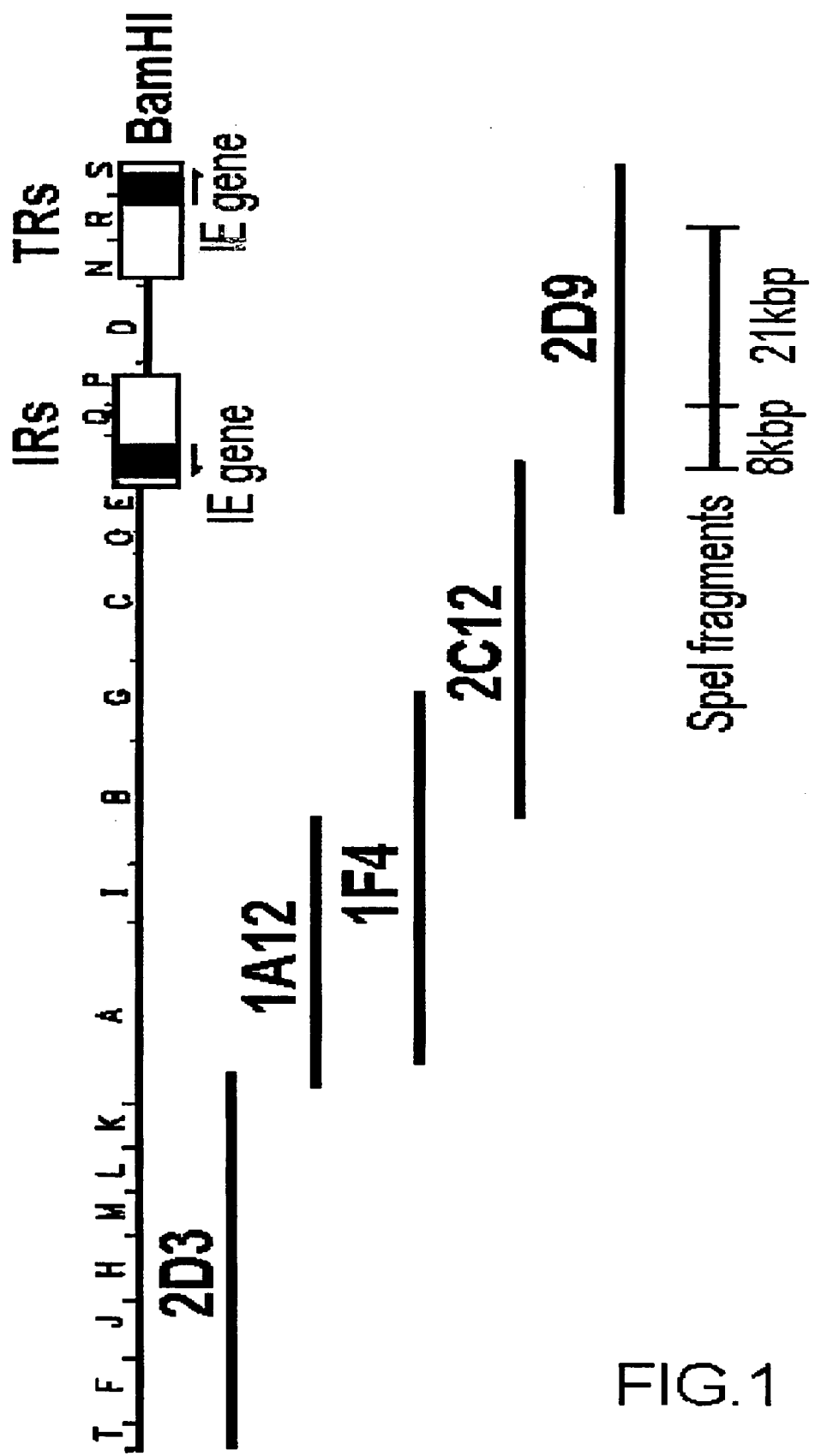
FIG. 1 shows a map of the EHV-1 genome with the position of five cosmid DNA inserts that restore a viable virus after cotransfection and recombination between their overlapping sequences. Deletions in the IE gene promoter were introduced into a 8 kb SpeI fragment of the IRs that was re-assembled with a 21 kb SpeI and used as such to replace cosmid 2D9 in the cotransfection experiment.

In a first embodiment of the invention, the promoter region is of the immediate early (IE) gene of the EHV virus. Other essential genes of which the promoters can be used are the genes involved in DNA replication (e.g. gene 57 in EHV-1 encoding the helicase/primase complex), or transactivators of immediate early genes such as gene 12 in EHV-1 or genes encoding essential structural components of the virion such as the glycoproteins gB, gH and gL in EHV-1 or other herpesviruses.

The sequence upstream of the transcription initiation start contains several elements that regulate expression of a gene. All these elements together are defined as the promoter. The core sequence of the promoter, also known as TATA-box, is located about 40 base pairs from the transcription start, although this structure may vary considerably from case to case. Other more or less conserved elements are located further upstream such as the CCAAT sequence and CG repeated motives. Some elements are specifically found in certain types of promoters, such as a TAATGARATTC consensus sequence in immediate early genes of herpesviruses. Also the sequence corresponding to the non-translated region upstream of the ATG start codon can be involved in promoter activity. Many of these elements have not yet been defined nor are fully understood how they interact with the so-called transcription factors as a result of which transcription of the gene is regulated.

For the purpose of the present invention, however, a promoter is defined as the sequence extending over several hundreds of base pairs upstream of the coding region of the gene with the most important part situated in the 200 base pairs preceding the transcription initiation site. Examples of sequences that contain promoters from essential genes can be retrieved from GenBank. The complete sequence for EHV-1 and EHV-4 have been deposited at GenBank under Accession No. M86664 and AF030027, respectively. For genes 57 and 12 from EHV-1, the promoter will be located between nucleotides 101.600–102.347 and 12.900–13.505, respectively.

Alternatively, promoter regions can be determined by nucleotide sequence analysis of DNA fragments that contain an essential gene, including the region upstream of the coding sequence.

A preferred embodiment of the invention is the endogenous promoter of the IE gene of EHV-1 of which one copy is located between nucleotide 118.590 and about 119.890 in the Inverted Repeat of the short segment (IRs).

It has been found according to the invention that the endogenous promoter region of essential genes can be more suitable for attenuating the virulence of EHV. Until now this has not been considered because the manipulation of an essential gene was assumed to be deleterious to efficient replication in the host.

The term "essential gene" as used herein is intended to encompass genes that are obligatory for replication in the host. "Gene" is used solely for the coding sequence, whereas "promoter region" refers to the regulatory sequences necessary for expression of the gene.

Preferred mutations according to the invention are deletions between 1 and about 500 bases at any position within the promoter region that reduce the level of expression of the essential gene that is located downstream and attenuates virulence of the pathogen. By no means does a deletion according to the present invention abolish the expression of the gene product.

For EHV-1, preferred deletions are deletion of the SacI—SacI fragment or the HindIII-ClaI fragment or the NdeI—NdeI fragment or the SphI—SphI fragment of the promoter region of the Immediate Early gene. Highly preferred is a deletion of the HindIII-ClaI fragment of the IE promoter region; this deletion abolishes virulence of the virus without affecting local replication in the host. An EHV-1 mutant comprising a deletion of the HindIII-ClaI fragment of the promoter region of its IE gene shows an exceptionally good level of attenuation without any negative effect on its replication, thus making this mutant highly suitable for use in a live vaccine.

As an alternative, fragments with a size between 1 and about 500 bases can be inserted in the endogenous promoter region, provided that said insertion does not abolish expression of the essential gene product. Such insertions according to the invention do not interfere with viral replication and have the advantage that they can lead to a desired level of reduction in virulence.

Substitutions can be made in the endogenous promoter of an essential viral gene varying from one or more nucleotides up to 500 base pairs provided that said substitution does not lead to loss of expression of the essential gene product. Substitutions according to the invention do not result in abolished replication of the virus in the host, but can lead to a desired level of attenuation.

Substitution according to the invention should not be confused with substitution of the complete promoter region by a cell, tissue or host specific promoter as described by Glazenburg et al. in U.S. Pat. No. 5,580,564. Glazenburg aims at choosing the cell, the tissue and/or the host such that the harmful characteristics of the microorganism are not expressed or are only expressed to an acceptable degree. The overall virulence of the virus is not decreased, but instead the localisation of the viral replication is limited to particular cells, tissues or hosts. Substitutions according to the invention are not intended to encompass such mutations into specific promoters that lead to a modified cell, tissue or host tropism.

Deletions can be introduced by the following methods. Based on the map of the promoter region, suitable restriction sites can be deduced to remove fragments of a defined size and at a defined position in the promoter. As an alternative, one could start at a single site and make progressive deletions in either one or two directions using the technique described by Henikoff (Gene 28, 351–359 (1984)). Also linker or PCR-mediated mutagenesis (Current Protocols in Molecular Biology, Eds. Ausubel et al., Chapter 8, John Whiley & Sons. Inc. (1996) can be used.

Mutations introduced in cloned subfragments can de transferred to the virus genome as for example described in Maniatis, T. et al. (1982) in "Molecular cloning", Cold Spring Harbor Laboratory; European Patent Application 74.808; Roizman, B. & Jenkins, F. J. (1987), Science 229, 1208; Higuchi, R. et al. (1988), Nucleic Acids Res. 16, 7351.

Briefly, this can be accomplished by constructing a recombinant DNA molecule for recombination with Equine herpesvirus DNA. Such a recombinant DNA molecule comprises vector DNA which may be derived from any suitable plasmid, cosmid, virus or phage, and contains Equine herpesvirus DNA of the region identified above.

Examples of suitable cloning vectors are plasmid vectors such as pBR322, the various pUC and Bluescript plasmids, cosmid vectors, e.g. THV, pJB8, MUA-3 and CosI, bacteriophages, e.g. lambda-gt-WES-lambda B, charon 28 and the M13 mp phages or viral vectors such as SV40, Bovine papillomavirus, Polyoma and Adeno viruses. Other vectors to be used can be retrieved from the Intelligenetics vector database accessible through website http://www.seqnet.dl.ac.uk.

A deletion to be introduced in the described region can be incorporated first in a recombinant DNA molecule carrying the promoter region of the essential gene of EHV by means of a restriction enzyme digest with one or more enzymes of which the cleavage sites are correctly positioned in the promoter region of the gene. Recircularization of the remaining recombinant DNA molecule would result in a derivative lacking at least part of the promoter region. Alternatively, progressive deletions can be introduced either in one or two directions starting from within the restriction enzyme cleavage site present within the sequence of the gene. Enzymes such as Bal31 or exonuclease III can be used for this purpose.

Recircularized molecules are transformed into *E. coli* cells and individual colonies can be analyzed by restriction mapping in order to determine the size of the deletion introduced into the promoter region. An accurate positioning of the deletion can be obtained by sequence analysis.

In case the insertion of a heterologous nucleic acid sequence is desired, the recombinant DNA molecule comprising the EHV essential gene may be digested with appropriate restriction enzymes to produce linear molecules, whereafter the heterologous nucleic acid sequence can be ligated to the linear molecules followed by recircularization of the recombinant DNA molecule.

Optionally, a deletion is introduced into the promoter region of the EHV gene concomitantly with the insertion of the heterologous nucleic acid sequence.

In case the method of in vivo homologous recombination is applied for the preparation of an EHV mutant according to the invention, the EHV sequences which flank the deleted gene sequences or the inserted heterologous nucleic acid sequences should be of appropriate length, e.g. 50–3000 bp, as to allow in vivo homologous recombination with the viral EHV genome to occur.

Subsequently, cells, for example, equine cells such as equine dermal cells (NBL-6) or cells from other species such as RK13, Vero and BHK cells can be transfected with EHV DNA in the presence of the recombinant DNA molecule containing the mutation flanked by appropriate EHV sequences whereby recombination occurs between the EHV sequences in the recombinant DNA molecule and the corresponding sequences in the EHV genome.

Recombinant viral progeny are thereafter produced in cell culture and can be selected, for example, genotypically or phenotypically, e.g. by hybridization. The selected EHV mutant can be cultured on a large scale in cell culture, whereafter EHV mutant-containing material can be collected therefrom.

The EHV-1 genome contains two copies of the Immediate Early gene, in opposite orientation. In this case, a convenient method for mutating the promoter is the construction of a set of cosmids harbouring fragments of the EHV genome, including only one of the two copies of the IE gene and its promoter region. This single copy of the promoter region can then be mutated in a routine manner. The set of cosmids is transfected into a confluent monolayer of host cells. Viruses will be formed by recombination and can be recovered from plaques formed in the monolayer. It is necessary to use one copy of the IE promoter region and corresponding gene for the preparation of a mutant according to the invention to prevent replacement of the mutation by the non-mutated promoter region. The mutant virus will restore a second identical copy of the mutated promoter region of the IE gene while assembling a functional full-size genome containing both inverted repeats flanking the Us.

It is standard procedure to test the efficacy and safety of a vaccine in vivo. Initial testing of mutant EHV viruses can be performed in the well-known mouse model as described by van Woensel et al., J. Virological Methods 54, 39–49, (1995) and Osterrieder et al., Virology 226, 243–251, (1996). Final testing of the safety and efficacy of the virus strain takes place in vivo in horses.

The mutation(s) in the endogenous promoter of one or more essential genes can be combined with one or more mutations in one or more other genes and/or their promoters. Examples of these are mutations creating a marker vaccine which allow differentiation of vaccinated animals from infected animals. This way a further optimisation of the vaccine's properties can be obtained.

The invention further relates to a nucleic acid molecule comprising the endogenous promoter region of an EHV essential gene and optionally one or more flanking sequences, which promoter region comprises one or more deletions, substitutions or insertions. The gene is, for example, an Immediate Early gene, or any other essential gene, such as those described hereinabove.

Specific deletions are deletions of the SacI—SacI fragment or the HindIII-ClaI fragment or the NdeI—NdeI fragment or the SphI—SphI fragment of the promoter region of the Immediate Early gene. Particularly preferred are deletions of the HindIII-ClaI fragment of the promoter region of the Immediate Early gene of EHV.

The nucleic acid molecule in a specific embodiment comprises the promoter region of EHV-1 or EHV-4, more specifically EHV-1.

This nucleic acid molecule can be incorporated into a recombinant DNA molecule, which is also part of the invention. The selection of suitable vectors to prepare the recombinant DNA molecule are well within the reach of the person skilled in the art.

In addition, the invention relates to a host cell harbouring such a recombinant DNA molecule.

The present invention further provides for a vaccine comprising an EHV mutant of the invention and a pharmaceutically acceptable carrier or diluent.

A live attenuated mutant according to the present invention can be used to vaccinate equines, particularly domestic and non-domestic, and more specifically horses. Vaccination with such a live vaccine is preferably followed by replication of the mutant within the inoculated host, which host will then elicit an immune response against EHV, and the animal inoculated with the EHV mutant according to the invention will be immune to infection by EHV. Thus, a mutant according to claim 1 can serve as a live vaccine.

For the preparation of a live vaccine, the recombinant EHV mutant according to the present invention can be grown on a cell culture, for example, of equine, rabbit, hamster or calf origin. The viruses thus grown can be harvested by collecting the tissue cell culture fluids and/or cells. The live vaccine may be prepared in the form of a suspension or may be lyophilised.

The vaccine according to the invention can be prepared using standard techniques available in the art. In general, the vaccine is prepared by mixing the virus with a pharmaceutically acceptable carrier or diluent.

For administration to animals, the EHV mutant according to the present invention can be given, inter alia, intranasally, intradermally, subcutaneously or intramuscularly.

Pharmaceutically acceptable carriers or diluents that can be used to formulate a vaccine according to the invention are sterile and physiologically compatible such as, for example, sterile water, saline, aqueous buffers such as alkali metal phosphates (e.g. PBS), alcohols, polyols and the like. In addition, the vaccine according to the invention may comprise other additives such as adjuvants, stabilizers, antioxidants, preservatives and the like.

Suitable adjuvants include, but are not limited to, aluminium salts or gels, carbomers, non-ionic blockcopolymers, tocopherols, monophosphoryl lipid A, muramyl dipeptide, oil emulsions (w/o or o/w), and cytokines. The amount of adjuvant added depends on the nature of the adjuvant itself.

Suitable stabilizers for use in a vaccine according to the invention are, for example, carbohydrates including sorbitol, mannitol, starch, sucrose, dextrin and glucose, proteins such as albumin or casein, and buffers like alkaline phosphates.

Suitable preservatives include, amongst others, thimerosal, merthiolate and gentamicin.

Live vaccines according to the invention comprise an effective amount of the afore-mentioned EHV mutant virus and a pharmaceutically acceptable carrier. The term "effective" as used herein is defined as the amount sufficient to induce an immune response in the target animal. The amount of virus will depend on the route of administration and the time of administration, as well as age, general health and diet of the subject to be vaccinated.

The dosages in which the live vaccines according to the invention can prevent infectious disease can be readily determined by routine trials with appropriate controls and are well within the routine skills of the practitioner.

The useful dosage to be administered will vary depending on the age, weight, mode of administration and type of pathogen against which vaccination is sought. A suitable dosage can be, for example, about $10^{3.0}$–$10^{7.0}$ pfu/animal.

According to a further aspect thereof, the invention provides a process for the preparation of EHV mutants, comprising transfecting a cell culture with a recombinant DNA molecule and EHV genomic DNA.

The invention thus provides for a method of genetically attenuating equine herpesviruses, comprising mutation of the endogenous promoter region of an essential gene, which mutation consists of one or more deletions, substitutions or insertions in the promoter region of an essential gene.

The present invention will be further illustrated in the non-limiting examples that follow. All molecular biological techniques that are used in the examples are standard procedures as, for example, described in Sambrook et al., "Molecular Cloning, A Laboratory Manual", Cold Spring Harbor Laboratory Press (1989). These techniques will not be described in detail.

EXAMPLES

Example 1

Construction of the Cosmid Set for Generating EHV-1 Virus

The SuperCos 1 cosmid vector kit was purchased from Stratagene (Catalog# 251301) and enzymes were purchased at New England Biolabs. The vector was further modified by adding extra restriction enzyme sites to it. For this a DNA linker was purchased from Pharmacia containing the following restriction sites: BamHI, I-SceI, PacI, AscI, EcoRV, PacI, AscI, I-SceI and BamHI. The SuperCos 1 vector and the linkers were both cut with BamHI. The BamHI digested vector was dephosphorylated with alkaline phosphatase after which the BamHI digested linker was ligated into the SuperCos 1 vector by T4 DNA ligase, all according to the manufacturer's instructions. The resulting vector was designated THM and used for cloning the EHV-1 inserts.

Viral DNA was obtained from the EHV-1 M8 strain, a pathogenic EHV-1 strain isolated from a horse with severe signs of an EHV-1 infection, but could be any pathogenic EHV-1 strain. This particular virus was grown in cultures of Vero cells and was recovered by centrifugation. The viral DNA was prepared by lysis with EDTA and SDS, phenol extraction and alcohol precipitation.

The first set of cosmids was constructed by digestion of the EHV-1 DNA with PacI. After phenol extraction of the M8 PacI digests, the ends were filled in with T4 DNA polymerase and then dephosphorylated with alkaline phosphatase. The cosmid vector THM was digested with EcoRV and the inserts were ligated into the vector with T4 DNA ligase.

The ligation mix was added to a packaging mix (Gigapack, Stratagene) according to manufacturer's instructions. The packaged DNA was added to a fresh overnight culture of E. coli DH1 and placed for 1 hour at 37° C. The bacteria suspension was then spread onto agar plates containing ampicillin. Plasmid DNA from all colonies was submitted to restriction enzyme analysis on the insert.

For the construction of other cosmids, the same procedure was followed except that the viral DNA was digested with AscI, AseI, RsrI, or NotI, and all ends were then filled in with T4 DNA polymerase and the inserts were ligated into the EcoRV site of the vector.

To obtain a third generation of cosmids, the viral DNA was sheared twice through a 19G needle, the ends were then filled in with T4 DNA polymerase, and after phenol extraction and precipitation, the inserts were cloned again into the EcoRV site of the cosmid vector THM. The vector with the inserts was then packed, put on bacteria and the colonies analyzed.

From all colonies obtained, the restriction maps were determined by multiple digestions. Then the location of the different clones was determined by comparing the restriction map of the clones with the restriction map of EHV-1 strain Ab4 (Telford et al, 1992).

Cosmids 2D3, 1A12, 1F4, 2C12 and 2D9 were selected such that the complete genome could be reconstituted by recombination between overlapping sequences (FIG. 1).

Viable virus was generated after transfecting EHV-1 inserts excised from the cosmids by digestion with 1-Scel (Boehringer) into cultures of equine dermal cells (ATCC number CCL-57) using the calcium phosphate method. Viral progeny were passaged and plaque purified on monolayers of rabbit kidney (RK13, ATCC number CCL-37) or other kidney cells that support viral replication.

Example 2

Introduction of Deletions into the Promoter of the IE Gene

The genome of EHV-1 contains two copies of the Immediate Early (IE) gene located in the repeated sequence elements IRs and TRs flanking the unique short region. Stable mutations affecting expression of the IE gene need to be introduced at both positions simultaneously before the new phenotype will be expressed.

Figure 2:
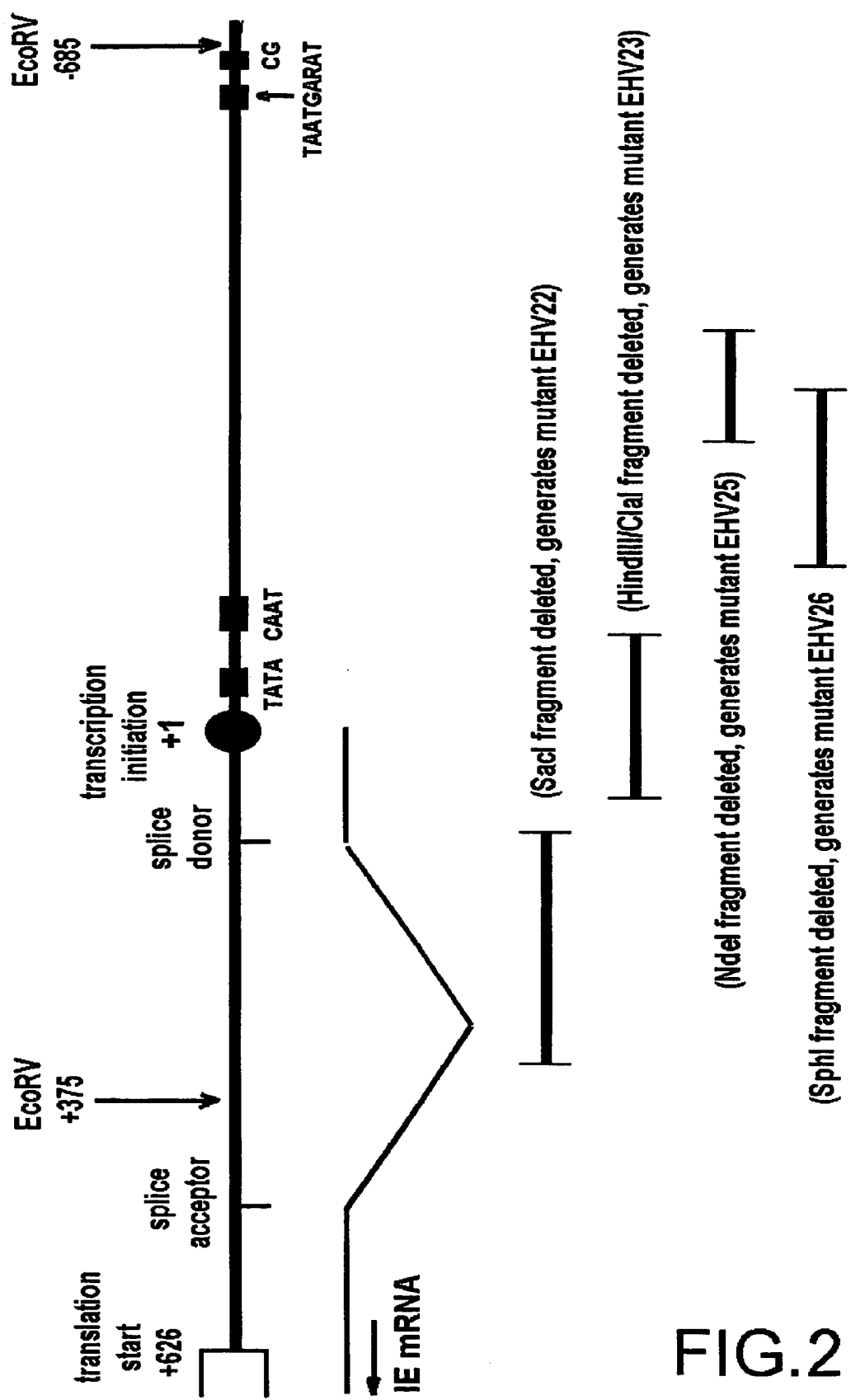
FIG. 2 shows a schematic layout of the promoter region of the IE gene in the IRs from EHV-1. Various sequence elements that may regulate transcription initiation are indicated. Below are shown the deletions that were introduced and the mutants that were generated by incorporating these deletions into the viral genome after co-transfection with the set of overlapping cosmid DNA inserts. Strain EHV24 was restored in a similar manner but contained no deletions in the promoter region.

Therefore, one of the cosmids named "2D9" was modified such that a fragment of about 7 kb at the right end of the TRs and containing a single copy of the IE gene, was deleted. This was obtained by subcloning the two SpeI fragments of 8 and 21 kb from 2D9 in pGEM-9Zf(−) (Promega) using the SpeI or SpeI/XbaI sites, respectively (FIG. 1). Insertion of the 21 kb fragment resulted in pEHV17 and restored a single SpeI site in which the 8 kb SpeI fragment subsequently can be inserted to regenerate a 29 kb EHV-1 fragment used for replacing 2D9 in the cosmid transfection described in Example 1. The 8 kb SpeI contains all of the coding sequence of the IE gene and about 2 kb of upstream sequences including the promoter of the IE gene. Mutations in the promoter region were introduced in a plasmid designated pEHV06 that contained a 2 kb subfragment from the 8 kb SpeI. This insert included a 1 kb EcoRV fragment which essentially represented the promoter and other regulatory elements located in the sequence upstream of the coding region of the IE gene (FIG. 2).

By selecting the proper restriction enzymes that had two site in the EcoRV fragment of pEHV06 and relatively near to each other, small deletions with an exact size could be introduced at various positions in the promoter sequence of the IE gene. The enzymes SacI, NdeI, SphI and a combination of ClaI and HindIII were suitable for this purpose. The deletions introduced in pEHV06 by digesting with each of these enzymes and recircularizing the plasmid DNA with T4 DNA ligase are represented in FIG. 2.

The mutated EcoRV inserts were exchanged with the original EcoRV insert in the 8 kb SpeI fragment and these were subsequently assembled with the 21 kb SpeI in pEHV17 resulting in plasmids that were designated pEHV22, pEHV23, pEHV25 and pHV26 for the deletions generated with the enzymes SacI, HindIII/ClaI, NdeI and SphI, respectively (FIG. 2). pEHV24 contained the re-assembled 8 and 21 kb SpeI fragments but without any deletion in the promoter region. These plasmids were used to replace 2D9 in the cotransfection of equine dermal cells with the cosmid inserts from 2D3, 1A12, 1F4 and 2C12, generating viable virus with defined small deletions in the promoter region of both copies of the IE gene. Viral progeny was plaque purified and amplified on RK13 cells. Presence and size of the deletions were confirmed by DNA blot analysis and PCR.

Mutant strains were designated EHV22, EHV23, EHV25 or EHV26 with the number corresponding to the plasmid used in the cotransfection experiment. Strain EHV24 represents the control virus and contains the non-mutated promoter region.

Cosmid derived mutant EHV strains 22, 25 and 26 and the control strain EHV24 grow to titers between 2 and $4 \times 10^6$ pfu/ml on RK13 cells, which is slightly less than the parent M8 strain that grows to titer of $5 \times 10^6$ pfu/ml. Strain EHV23 replicated less efficiently and resulted in titers of about $2 \times 10^5$ pfu/ml.

Example 3

Analysis of Virulence in Mice

Infection with EHV-1 can cause pyrexia and clinical signs of respiratory disease, but most important is the induction of abortion. However, in view of the complexity of vaccination trials in pregnant horses, models have been developed in mice measuring the pathogenicity of EHV-1 strains based on weight reduction (van Woensel et al., J. Virological Methods 54, 39–49, (1995); Osterrieder et al., Virology 226, 243–251, (1996).

Mice that are 4–5 weeks of age are inoculated intranasally with a dose of $10^{6.5}$ pfu per animal. Body weights are determined on the 9 days following infection and the weight gain as percentage of the weight at day 0 is plotted in a graph. The degree of pathogenicity of various EHV-1 strains is deduced from the position of resulting curves relative to each other. Significant losses in body weight, particularly at day 3 and 4 after infection, correlate with high virulence of the strain of interest. Series of EHV-1 isolates carrying deletions in the IE promoter region (see Example 2) can be analyzed for virulence by comparison with the parent M8 strain or cosmid generated EHV-1 virus containing the intact promoter sequence.

Example 4

Analysis of Virulence in Horses

Although pathogenicity of individual EHV-1 strains using the mouse model can be correlated with behavior in the natural host, more conclusive evidence can be obtained from vaccination trials in horses. In addition, the level of protection against challenge infection and ultimately in preventing abortion in pregnant mares can only be established in the target animal.

The exeriment was performed in four conventional colts at the age of about one year and previously tested for the absence of EHV-1 serum antibodies. Animals were divided in groups of two, one group receiving mutant strain EHV23, the other receiving mutant strain EHV24. The colts were inoculated intranasally with a single dose of about $5 \times 10^5$ pfu, reconstituted in 2 ml Unisolve diluent and applying 1 ml in each nostril. Following 10 days, the animals were monitored for clinical reactions. Antibodies were measured at several time points either by virus-neutralisation or using a complement-fixing antibody assay. Infected blood leucocytes (viremia) and excreted virus in nasal swabs were determined by titration.

After three weeks, a fifth EHV-1 seronegative horse was added, and two weeks later, all five horses were challenged intranasally with $7 \times 10^5$ pfu of the pathogenic EHV-1 AB4p strain. The animals were again monitored for clinical reactions, virus excretion and infected blood leucocytes.

The horses vaccinated intranasally with a high dose of mutant strain EHV23 showed virtually no signs of disease, whereas horses vaccinated with mutant control strain EHV24 showed severe signs of EHV-1 infection, including fever and ocular or nasal discharges during several days. Both mutant strains were obtained in an identical way, in case of EHV23 introducing a 160 bp deletion in the IE promoter and in case of EHV24 no deletion at all(see example 2). EHV24 strain thus represents the control virus, containing the non-mutated IE promoter. Surprisingly, both strains were replicating in the nasal cavity, although it appeared that replication of the EHV23 strain was slightly delayed.

Challenge of all horses with EHV-1 strain AB4p did not induce significant signs of disease in the animals that had been previously inoculated with strain EHV23 or EHV24. No viremia was detected in any of the horses inoculated with either strain EHV23, or EHV24, which indicates a solid systemic protection of these animals against a challenge infection with the EHV-1 AB4p strain.

The invention claimed is:

1. An equine herpes virus (EHV) mutant, having at least one mutation comprising one or more deletions, substitutions or insertions introduced into the endogenous promoter region of the Immediate Early (IE) gene or the EHV, whereby the level of expression of an essential gene located downstream from the mutation is reduced and the virulence of the EHV is attenuated.

2. The EHV mutant of claim 1, wherein one or more deletions of between 1 and about 500 bases are introduced into the promoter region.

3. The EHV mutant of claim 1, wherein the mutant virus is the EHV-1 virus or the EHV-4 virus.

4. The EHV mutant of claim 1, further comprising one or more mutations in one or more other genes and/or their promoters.

5. The EHV mutant of claim 1, comprising a deletion of the SacI—SacI fragment, the HindIII-ClaI fragment, the NdeI—NdeI fragment or the SphI—SphI fragment of the promoter region of the Immediate Early gene.

6. An isolated nucleic acid molecule comprising the endogenous promoter region of the Immediate Early gene from EHV and optionally one or more flanking sequences, which promoter region comprises a deletion or the SacI—SacI fragment, the HindIII-ClaI fragment, the NdeI—NdeI fragment or the SphI—SphI fragment, thereof.

7. The nucleic acid molecule of claim 6, wherein the EHV is EHV-1 or EHV-4.

8. A recombinant DNA molecule comprising the nucleic acid molecule of claim 6.

9. A host cell comprising the DNA molecule of claim 8.

10. A vaccine comprising the EHV mutant of claim 2 and a pharmaceutically acceptable carrier or diluent.

11. A vaccine comprising the EHV mutant of claim 2 and a pharmaceutically acceptable carrier or diluent.

12. A method of genetically attenuating EHV, comprising the step of mutating the endogenous promoter region of the IE gene, which mutation comprises one or more deletions, substitutions or insertions, whereby the level of expression of an essential gene located downstream from the mutation is reduced and the virulence of the EHV is attenuated.

13. The method of claim 12, wherein the EHV is EHV-1 or EHV-4.

14. A vaccine comprising the EHV mutant of claim 1, and a pharmaceutically acceptable carrier or diluent.

15. A vaccine comprising the EHV mutant of claim 2, and a pharmaceutically acceptable carrier or diluent.

16. The EHV mutant of claim 5, wherein said deletion is or the HindIII-ClaI fragment.

17. The nucleic acid molecule of claim 6, wherein said deletion is of the HindIII-ClaI fragment.

18. A vaccine comprising the EHV mutant of claim 5 and a pharmaceutically acceptable carrier or diluent.

19. A vaccine comprising the EHV mutant of claim 16 and a pharmaceutically acceptable carrier or diluent.

* * * * *